United States Patent [19]
Gwynn et al.

[11] Patent Number: 5,962,303
[45] Date of Patent: Oct. 5, 1999

[54] TOPOISOMERASE III

[75] Inventors: Michael N. Gwynn, Chester Springs; Howard Kallendar, King of Prussia, both of Pa.

[73] Assignee: SmithKline Beecham Corporation, Philadelphia, Pa.

[21] Appl. No.: 08/949,584

[22] Filed: Oct. 14, 1997

Related U.S. Application Data

[60] Provisional application No. 60/028,603, Oct. 15, 1996.

[51] Int. Cl.$^6$ .............................. C12N 1/00; C12N 5/10; C12N 9/90; C12N 15/61; C12N 15/63
[52] U.S. Cl. .................. 435/233; 435/320.1; 435/252.3; 435/254.11; 435/325; 436/23.2; 436/24.32
[58] Field of Search ................................ 435/233, 252.3, 435/254.11, 320.1, 455, 468, 471; 536/23.2, 24.32

[56] References Cited

U.S. PATENT DOCUMENTS 5,004,758  4/1991  Boehm et al. ........................ 514/283

OTHER PUBLICATIONS

Lerner, et al: "High Throughput Screen for Inhibitors of Bacterial DNA Topoisomerase I Using the Scintillation Proximity Assay" *Journal of Biomolecular Screening*, vol. 1, No. 3; pp. 135–143 (1996).
Snewin, et al.: "Cloning and Characterisation of a gene from *Plasmodium vivax* and *P. knowlesi*: homology with valine–tRNA synthetase" *Gene* vol. 173 No. 2 (1996) pp. 137–145.
Brown, et al: "A Sign Inversion Mechanism for Enzymatic Supercoiling of DNA" *Science* vol. 206, pp. 1081–1083 (1979).
Yoshimora, et al: "*Bacillus subtilis* secretes a foreign protein by the signal sequence of *Bacillus amyloliquefaciens* neutral protease" *Appl. Microbiol* vol. 23, pp. 250–256 (1986).
Huang, et al: "DNA Topology and Its Biological Effects" *ColdSpring Harbor Laboratory Press* (1990), pp. 265–284.
Kato, et al.: "Purification and Characterization of DNA Topoisomerase IV in *Escherichia coli*" *Journal of Biological Chemistry* vol. 267, No. 3, pp. 25676–25684 (1992).
Hsieh, et al: "Mechanistic Aspects of Type–II DNA Topoisomerase" *ColdSpring Harbor Laboratory Press* (1990), pp. 243–263.
Morton, T.M. et al. "DNA sequence and units of transcription of the conjugative transfer gene complex (trs) of *Staphylococcus aureus* plasmid pGO1." Journal of Bacteriology (Jul. 1993), vol. 175, No. 14, pp. 4436–4447, Jul. 1993.
Kim, et al.: "Identification of the Yeast TOP3 Gene Product as a Single Strand–specific DNA Topoisomerase" *Journal of Biological Chemistry*, vol. 267, No. 24, pp. 17178–17185 (1992).

Hanai, et al.: "Human TOP3: A single–copy gene encoding DNA topoisomerase III" *Proc. Natl. Acad. Sci. USA* vol. 93, pp. 3653–3657 (1996).
Siedlecki, et al.: "Characterization of a prokaryotic topoisomerase I activity in chloroplast extracts from spinach" *Nucleic Acids Research* vol. 11, pp. 1523–153b (1983).
Kikuchi, et al: "DNA Topology and Its Biological Effect" *ColdSpring Harbor Laboratory Press* (1990), pp. 285–298.
De La Tour, et al.: "Reverse Gyrase in Thermophilic Eubacteria" *Journal of Bacteriology* vol. 173, No. 12, pp. 3921–3923 (1991).
Slesarev, et al.: "DNA Topoisomerase III from Extremely Thermophilic Archaebacteria" *Journal of Biological Chemistry* vol. 266, No. 19, pp. 12321–12328 (1991).
Neil Osheroff: "Biochemical Basis for the Interactions of Type I and Type II Topoisomerases with DNA" *Pharmac. Ther.* vol. 41, pp. 223–241 (1989).
Karl Drlica: "Biology of Bacterial Deoxyribonucleic Acid Topoisomerase" *Microbiological Reviews* vol. 48, No. 4, pp. 273–289 (1984).
Glisson, et al: "DNA Topoisomerase II: A Primer on the Enzyme and its Unique Role as a Multidrug Target in Cancer Chemotherapy" *Pharmac. Ther.* vol. 32, pp. 89–106 (1987).
Bodley, et al.: "Topoisomerases as Novel Targets for Cancer Chemotherapy" *Bio/technology* vol. 6 pp. 1315–1319 (1988).
Leroy F. Liu: "DNA Topoisomerase Poisons as Antitumor Drugs" *Annu. Rev. Biochem.* vol. 58, pp. 351–375 (1989).
Amy Luttinger: "The Twisted 'life' of DNA in the cell: bacterial topoisomerases" *Molecular Microbiology* vol. 15(4), pp. 601–606 (1995).
Berlani, et al.: "Transfer RNA genes in the cap–oxil region of yeast mitochondrial DNA" *Nucleic Acids Research* vol. 8, No. 21 (1980).
Joaquim Roca: "The mechanisms of DNA topoisomerase" *TIBS* vol. 20, pp. 156–160 (1995).

*Primary Examiner*—Robert A. Wax
*Assistant Examiner*—Gabriele E. Bugaisky
*Attorney, Agent, or Firm*—Edward R. Gimmi; William T. King; Arthur E. Jackson

[57] ABSTRACT

Topoisomerase III polypeptides and DNA and RNA encoding such Topoisomerase III polypeptides and a procedure for producing such polypeptides by recombinant techniques is disclosed. Also disclosed are methods for utilizing such Topoisomerase III for the treatment of infection, particularly bacterial infections. Antagonists against such Topoisomerase III and their use as a therapeutic to treat infections, particularly bacterial infections are also disclosed. Also disclosed are diagnostic assays for detecting diseases related to the presence of Topoisomerase III nucleic acid sequences and the polypeptides in a host. Also disclosed are diagnostic assays for detecting polynucleotides encoding Streptococcal Topoisomerase III and for detecting the polypeptide in a host.

29 Claims, 2 Drawing Sheets

FIGURE 1. *S. pneumoniae* Topoisomerase III DNA Sequence (SEQ ID NO: 1)

```
  1  GATGTTCGTT GAAGCCGAAC TGAAGCCGAC CGGTCTGGAG CGAGCCGAAG
 51  CCCAGGCCAT CGCCGACGCG GTGCGCAACC AGACCGGCAC CGTCACCGAA
101  GAAGCCAAGC CCAGCACGCA GGCCAGCCCG TTGCTGTACG ACCTGACCAC
151  GCTGCAACGC GAAGCCAACT CGGCGCTTCGG CTTCAGCGCC AAGACCACGC
201  TGTCGCTGGC ACAGGGCGCTA TACGAAAAAC ACAAGGGCGCT GACCTACCCG
251  CGGACCGATT CACGCGCCCT GCCTGAAGAC GCCCGGCCCG CTGAAGGCTT
301  GACCGTCGGC GTGCTGGCCG AGGGCGACCT GCCCGGCCCG CTGAAGGCTT
351  TGTCGGCTCA CGCCGAAAAG GCGCTGAAAG AGGGTTACAT CAAACCCAAC
401  AAGCGCGTGT TCGACAACGC CAAGGTGTCG GACCACTTCG CC
```

FIGURE 2. Topoisomerase III predicted amino acid sequence (SEQ ID NO: 2)

1    MFVEAELKPT GLERAEAQAI ADAVRNQTGT VTEEAKPSTQ ASPLLYDLTT

51   LQREANSRFG FSAKTTLSLA QALYEKHKAL TYPRTDSRAL PEDYLGVVKQ

101  TVGVLAEGDL PGPLKALSAH AEKALKEGYI KPNKRVFDNA KVSDHFA

TOPOISOMERASE III

RELATED APPLICATION

This application claims benefit of U.S. Provisional Application Ser. No. 60/028,603, filed Oct. 15, 1996.

FIELD OF THE INVENTION

This invention relates, in part, to newly identified polynucleotides and polypeptides; variants and derivatives of these polynucleotides and polypeptides; processes for making these polynucleotides and these polypeptides, and their variants and derivatives; agonists and antagonists of the polypeptides; and uses of these polynucleotides, polypeptides, variants, derivatives, agonists and antagonists. In particular, in these and in other regards, the invention relates to polynucleotides and polypeptides of bacterial "Topoisomerase III".

BACKGROUND OF THE INVENTION

Among the more effective antibiotics are those that interfere with common modes of bacterial gene expression, regulation or activity. Recently, the supercoiling of DNA had been suggested as a possible mode of virulence gene regulation. Local increases or decreases in DNA density, due to supercoiling, have been associated with responses to various environmental conditions such as, temperature, anaerobiosis, and osmolarity. Appropriate regulation of the accessibility of groups of genes to components of the transcriptional apparatus by increasing or decreasing supercoiling of spacially organized genes may represent an infecting pathogen's effective response to such environmental conditions. Enzymes, such as DNA topoisomerases including type 1 topoisomerases and DNA gyrases, have been identified which function to effect the levels of DNA supercoiling. Such enzymes represent useful targets against which to screen compounds as potential antibiotics.

DNA transformations performed by DNA topoisomerases are accomplished by the cleavage of either a single strand or both strands. The unit change in the Linking number (Lk) resulting from such transformations is the best operational distinction between the two classes of topoisomerases (P. O. Brown & N. R. Cozzarelli, *Science* 206:1081–1083 (1979)). The linking number (Lk) is the algebraic number of times one strand crosses the surface stretched over the other strand. DNA topoisomerases whose reactions proceed via a transient single-stranded break and changing the Lk in steps of one are classified as type 1, while enzymes whose reactions proceed via double-stranded breaks and changing the Lk in steps of two are classified as type 2.

Members of type 2 topoisomerase family include DNA gyrase, bacterial DNA topoisomerase IV, T-even phage DNA topoisomerases, eukaryotic DNA topoisomerase II, and thermophilic topoisomerase II from *Sulfolobus acidocaldarius* (see: A. Kikuchi et al., *Syst. Appl. Microbiol.* 7:72–78 (1986); J. Kato et al., *J. Biol. Chem.* 267:25676–25684 (1992); W. M. Huang in DNA Topology and Its Biological Effects (N. R. Cozzarelli and J. C. Wang, eds., Cold Spring Harbor Laboratory Press, New York, 1990), pp. 265–284; T.-S Hsieh in DNA Topology and Its Biological Effects (N. R. Cozzarelli and J. C. Wang, eds., Cold Spring Harbor Laboratory Press, New York, (1990), pp. 243–263)). The coding sequences of a dozen or so type 2 enzymes have been determined, and the data suggest that all these enzymes are evolutionary and structurally related. Topological reactions catalyzed by type 2 topoisomerases include introduction of negative supercoils into DNA (DNA gyrase), relaxation of supercoiled DNA, catenation (or decatenation) of duplex circles, knotting and unknotting of DNA.

The family of type I topoisomerases comprises bacterial topoisomerase I, *E. coli* topoisomerase III, *S. cerevisiae* topoisomerase III (R. A. Kim & J. C. Wang, *J. Biol. Chem.* 267:17178–17185 (1992), human topoisomerase III (Hanai et al., *Proc. Natl. Acad. Sci.* 93:3653–3657 (1996)), the type 1 topoisomerase from chloroplasts that closely resembles bacterial enzymes (J. Siedlecki et al., *Nucleic Acids Res.* 11:1523–1536 (1983), thermophilic reverse gyrases (A. Kikuchi, In DNA: "Topology and Its Biological Effects" (N. R. Cozzarelli and J. C. Wang, eds., Cold Spring Harbor Laboratory Press, New York, 1990, pp. 285–298); C. Bouthier de la Tour et al., *J. Bact.* 173:3921–3923 (1991), thermophilic *D. amylolyticus* topoisomerase III (A. I. Slesarev et al., *J. Biol. Chem.* 266:12321–12328 (1991), nuclear topoisomerases I and closely related enzymes from mitochondria and poxviruses (N. Osheroff, *Pharmac. Ther.* 41:223–241 (1989)). With respect to the mechanism of catalysis these topoisomerases can be divided into two groups. Group A consists of enzymes that require a divalent cation for activity, and form a transient covalent complex with the 5'-phosphoryl termini (prokaryotic type 1 topoisomerases, *S. cerevisiae* topoisomerase III, and human topoisomerase III). Group B includes type 1 topoisomerases that do not require a divalent cation for activity, and bind covalently to the 3'-phosphoryl termini (nuclear topoisomerases I, enzymes from mitochondria and poxviruses commonly called eukaryotic topoisomerases I). Type 1 topoisomerases can carry out the following topological reactions: they relax supercoiled DNA (except of reverse gyrases), catenate (or decatenate) single-stranded circular DNAs or duplexes providing that at least one of the molecules contains a nick or gap, or interact with single-stranded circles to introduce topological knots (type 1-group A topoisomerases). Reverse gyrase, belonging to type 1-group A topoisomerases, is the only topoisomerase shown to be able to introduce positive supercoils into cDNA.

Research on DNA topoisomerases has progressed from DNA enzymology to developmental therapeutics. Bacterial DNA topoisomerase II is an important therapeutic target of quinolone antibiotics; mammalian DNA topoisomerase II is the cellular target of many potent antitumor drugs (K. Drlica, *Microbiol. Rev.* 48:273–289 (1984) and *Biochemistry* 27:2253–2259 (1988); B. S. Glisson & W. E. Ross, *Pharmacol. Ther.* 32:89–106 (1987); A. L. Bodley & L. F. Liu, *Biotechnology* 6:1315–1319 (1988); L. F. Liu, *Annu. Rev. Biochem.* 58:351–375 (1989)). These drugs, referred to as topoisomerase II poisons, interfere with the breakage-rejoining reaction of type II topoisomerase by trapping a key covalent reaction intermediate, termed the cleavable complex. Mammalian topoisomerase I is the cellular target of the antitumor drug topotecan (U.S. Pat. No. 5,004,758), which also traps the covalent reaction intermediate.

As mentioned above, bacterial type I topoisomerases (topoisomerase I & III) are enzymes that alter DNA topology and are involved in a number of crucial cellular processes including replication, transcription and recombination (Luttinger, A., *Molecular Microbiol.* 15(4): 601–608 (1995). These enzymes act by transiently breaking one strand of DNA, passing a single or double strand of DNA through the break and finally resealing the break. Cleavage of the DNA substrate forms a covalent linkage between a tyrosine residue of the enzyme and the 5' end of the DNA chain at the cleavage site (Roca, J. A., *TIBS* 20:156–160 (1995).

Enzyme inhibition which leads to the stabilization of the covalent-enzyme-DNA complex (cleavable complex), will invoke chromosomal damage, and bacterial cell death. Furthermore, this mechanism has the potential of leading to cell death by virtue of a single inhibition event. A small molecular weight inhibitor, which acts by stabilization of the cleavable complex may act on both topoisomerase I and III because of the extensive amino acid sequence similarity between them, particularly in the region of their active sites. The likelihood of future high level resistance to such agents arising from point mutation may therefore be low.

Inhibitors of type I topoisomerases, for example, those able to stabilize the protein in a covalent complex with DNA would be lethal or inhibitory to the bacterium and thereby have utility in anti-bacterial therapy. It is particularly preferred to employ Streptococcal genes and gene products as targets for the development of antibiotics. The Streptococci make up a medically important genera of microbes. They are known to produce two types of disease, invasive and toxigenic. Invasive infections are characterized generally by abscess formation effecting both skin surfaces and deep tissues. S. pneumoniae is the second leading cause of bacteremia in cancer patients. Osteomyelitis, septic arthritis, septic thrombophlebitis and acute bacterial endocarditis are also relatively common. There are at least three clinical conditions resulting from the toxigenic properties of Streptococci. The manifestation of these diseases result from the actions of exotoxins as opposed to tissue invasion and bacteremia. These conditions include: Streptococcal food poisoning, scalded skin syndrome and toxic shock syndrome.

SUMMARY OF THE INVENTION

Toward these ends, and others, it is an object of the present invention to provide polypeptides, inter alia, that have been identified as novel Topoisomerase III by homology between the amino acid sequence set out in FIG. 2 (SEQ ID NO: 2) and known amino acid sequences of other proteins such as *Bacillus subtilis* topoisomerase I which is 25.2% identical and 42.2% similar to the sequence in FIG. 2.

It is a further object of the invention, moreover, to provide polynucleotides that encode Topoisomerase III, particularly polynucleotides that encode the polypeptide herein designated bacterial Topoisomerase III.

In a particularly preferred embodiment of this aspect of the invention the polynucleotide comprises the region encoding Topoisomerase III in the sequence set out in FIG. 1 (SEQ ID NO: 1).

In another particularly preferred embodiment of the present invention there is a novel Topoisomerase III protein from *Streptococcus pneumoniae* comprising the amino acid sequence of (SEQ ID NO: 2), or a fragment, analogue or derivative thereof.

In accordance with this aspect of the present invention there is provided an isolated nucleic acid molecule encoding a mature polypeptide expressible by the *Streptococcus pneumoniae* polynucleotide contained in deposited strain NCIMB deposit number 40794.

In accordance with this aspect of the invention there are provided isolated nucleic acid molecules encoding Topoisomerase III, particularly Streptococcal Topoisomerase III, including mRNAs, cDNAs, genomic DNAs and, in further embodiments of this aspect of the invention, biologically, diagnostically, clinically or therapeutically useful variants, analogs or derivatives thereof, or fragments thereof, including fragments of the variants, analogs and derivatives.

Among the particularly preferred embodiments of this aspect of the invention are naturally occurring allelic variants of Topoisomerase III.

In accordance with this aspect of the invention there are provided novel polypeptides of Streptococcal origin referred to herein as Topoisomerase III as well as biologically, diagnostically or therapeutically useful fragments thereof, as well as variants, derivatives and analogs of the foregoing and fragments thereof.

It also is an object of the invention to provide Topoisomerase III polypeptides, particularly bacterial Topoisomerase III polypeptides, that may be employed for therapeutic purposes, for example, to treat disease, including treatment by conferring host immunity against bacterial infections, such as Streptococcal infections.

In accordance with yet a further aspect of the present invention, there is provided the use of a polypeptide of the invention, in particular a fragment thereof, for therapeutic or prophylactic purposes, for example, as an antibacterial agent or a vaccine.

In accordance with another aspect of the present invention, there is provided the use of a polynucleotide of the invention for therapeutic or prophylactic purposes, in particular genetic immunization.

Among the particularly preferred embodiments of this aspect of the invention are variants of Topoisomerase III polypeptide encoded by naturally occurring alleles of the Topoisomerase III gene.

It is another object of the invention to provide a process for producing the aforementioned polypeptides, polypeptide fragments, variants and derivatives, fragments of the variants and derivatives, and analogs of the foregoing.

In a preferred embodiment of this aspect of the invention there are provided methods for producing the aforementioned Topoisomerase III polypeptides comprising culturing host cells having expressibly incorporated therein an exogenously-derived Topoisomerase III-encoding polynucleotide under conditions for expression of Topoisomerase III in the host and then recovering the expressed polypeptide.

In accordance with another object the invention there are provided products, compositions, processes and methods that utilize the aforementioned polypeptides and polynucleotides, inter alia, for research, biological, clinical and therapeutic purposes.

In accordance with yet another aspect of the present invention, there are provided inhibitors of such polypeptides, useful as antibacterial agents. In particular, there are provided antibodies against such polypeptides.

In accordance with certain preferred embodiments of this and other aspects of the invention there are probes that hybridize to bacterial Topoisomerase III sequences useful for detection of bacterial infection.

In certain additional preferred embodiments of this aspect of the invention there are provided antibodies against Topoisomerase III polypeptides. In certain particularly preferred embodiments in this regard, the antibodies are selective for Streptococcal Topoisomerase III.

In accordance with another aspect of the present invention, there are provided Topoisomerase III agonists. Among preferred agonists are molecules that mimic Topoisomerase III, that bind to Topoisomerase III-binding molecules, and that elicit or augment Topoisomerase III-induced responses. Also among preferred agonists are molecules that interact with Topoisomerase III encoding genes or Topoisomerase III polypeptides, or with other modulators of Topoisomerase III activities, and thereby potentiate or augment an effect of Topoisomerase III or more than one effect of Topoisomerase III and which are also preferably bacteriostatic or bacteriocidal.

In accordance with yet another aspect of the present invention, there are provided Topoisomerase III antagonists. Among preferred antagonists are those which bind to Topoisomerase III so as to inhibit the binding of Topoisomerase III-binding molecules or to stabilize the complex formed between Topoisomerase III and Topoisomerase III binding molecule to prevent further biological activity arising from the Topoisomerase III. Also among preferred antagonists are molecules that bind to or interact with Topoisomerase III so as to inhibit an effect of Topoisomerase III or more than one effect of Topoisomerase III or which prevent expression of Topoisomerase III and which are also preferably bacteriostatic or bacteriocidal.

In a further aspect of the invention there are provided compositions comprising a Topoisomerase III polynucleotide or a Topoisomerase III polypeptide for administration to cells in vitro, to cells ex vivo and to cells in vivo, or to a multicellular organism. In certain preferred embodiments of this aspect of the invention, the compositions comprise a Topoisomerase III polynucleotide for expression of a Topoisomerase III polypeptide in a host organism to raise an immunological response, preferably to raise immunity in such host against Streptococci or related organisms.

Other objects, features, advantages and aspects of the present invention will become apparent to those of skill from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

BRIEF DESCRIPTION OF THE DRAWINGS

The following drawings depict certain embodiments of the invention. They are illustrative only and do not limit the invention otherwise disclosed herein.

FIG. 1 shows the polynucleotide sequence of *Streptococcus pneumoniae* Topoisomerase III (SEQ ID NO: 1).

FIG. 2 shows the amino acid sequence of *Streptococcus pneumoniae* Topoisomerase III (SEQ ID NO: 2) deduced from the polynucleotide sequence of FIG. 1 (SEQ ID NO: 1).

GLOSSARY

The following illustrative explanations are provided to facilitate understanding of certain terms used frequently herein, particularly in the Examples. The explanations are provided as a convenience and are not limitative of the invention.

Topoisomerase III-BINDING MOLECULE, as used herein, refers to molecules or ions which bind or interact specifically with Topoisomerase III polypeptides or polynucleotides of the present invention, including, for example enzyme substrates, such as supercoiled DNA, cell membrane components and classical receptors. Binding between polypeptides of the invention and such molecules, including binding or interaction molecules may be exclusive to polypeptides of the invention, which is preferred, or it may be highly specific for polypeptides of the invention, which is also preferred, or it may be highly specific to a group of proteins that includes polypeptides of the invention, which is preferred, or it may be specific to several groups of proteins at least one of which includes a polypeptide of the invention. Binding molecules also include antibodies and antibody-derived reagents that bind specifically to polypeptides of the invention.

GENETIC ELEMENT generally means a polynucleotide comprising a region that encodes a polypeptide or a polynucleotide region that regulates replication, transcription or translation or other processes important to expression of the polypeptide in a host cell, or a polynucleotide comprising both a region that encodes a polypeptide and a region operably linked thereto that regulates expression. Genetic elements may be comprised within a vector that replicates as an episomal element; that is, as a molecule physically independent of the host cell genome. They may be comprised within plasmids. Genetic elements also may be comprised within a host cell genome; not in their natural state but, rather, following manipulation such as isolation, cloning and introduction into a host cell in the form of purified DNA or in a vector, among others.

HOST CELL is a cell which has been transformed or transfected, or is capable of transformation or transfection by an exogenous polynucleotide sequence.

IDENTITY or SIMILARITY, as known in the art, are relationships between two polypeptide sequences or two polynucleotide sequences, as determined by comparing the sequences. In the art, identity also means the degree of sequence relatedness between two polypeptide or two polynucleotide sequences as determined by the match between two strings of such sequences. Both identity and similarity can be readily calculated (*Computational Molecular Biology*, Lesk, A. M., ed., Oxford University Press, New York, 1988; *Biocomputing: Informatics and Genome Projects*, Smith, D. W., ed., Academic Press, New York, 1993*Computer Analysis of Sequence Data*, Part I, Griffin, A. M., and Griffin, H. G., eds., Humana Press, New Jersey, 1994: *Sequence Analysis in Molecular Biology*, von Heinje, G., Academic Press, 1987; and *Sequence Analysis Primer*, Gribskov, M. and Devereux, J., eds., M Stockton Press, New York, 1991). While there exist a number of methods to measure identity and similarity between two polynucleotide or two polypeptide sequences, both terms are well known to skilled artisans (*Sequence Analysis in Molecular Biology*, von Heinje, G., Academic Press, 1987; *Sequence Analysis Primer*, Gribskov, M. and Devereux, J., eds., M Stockton Press, New York, 1991; and Carillo, H., and Lipman, D., SIAM *J. Applied Math.*, 48:1073 (1988). Methods commonly employed to determine identity or similarity between two sequences include, but are not limited to those disclosed in Carillo, H., and Lipman, D., SIAM *J. Applied Math.*, 48:1073 (1988). Preferred methods to determine identity are designed to give the largest match between the two sequences tested. Methods to determine identity and similarity are codified in computer programs. Preferred computer program methods to determine identity and similarity between two sequences include, but are not limited to, GCG program package (Devereux, J., et al., *Nucleic Acids Research* 12(1):387 (1984)), BLASTP, BLASTN, and FASTA (Atschul, S. F. et al., *J. Mol. Biol.* 215:403 (1990)).

ISOLATED means altered "by the hand of man" from its natural state; i.e., that, if it occurs in nature, it has been changed or removed from its original environment, or both. For example, a naturally occurring polynucleotide or a polypeptide naturally present in a living organism in its natural state is not "isolated," but the same polynucleotide or polypeptide separated from the coexisting materials of its natural state is "isolated", as the term is employed herein. For example, with respect to polynucleotides, the term isolated means that it is separated from the chromosome and cell in which it naturally occurs. As part of or following isolation, such polynucleotides can be joined to other polynucleotides, such as DNAs, for mutagenesis, to form fusion proteins, and for propagation or expression in a host, for instance. The isolated polynucleotides, alone or joined to other polynucleotides such as vectors, can be introduced into host cells, in culture or in whole organisms. Introduced into host cells in culture or in whole organisms, such DNAs still would be isolated, as the term is used herein, because they would not be in their naturally occurring form or environment. Similarly, the polynucleotides and polypeptides may occur in a composition, such as media formulations, solutions for introduction of polynucleotides or polypeptides, for example, into cells, compositions or solutions for chemical or enzymatic reactions, for instance, which are not naturally occurring compositions, and, therein remain isolated polynucleotides or polypeptides within the meaning of that term as it is employed herein.

POLYNUCLEOTIDE(S) generally refers to any polyribonucleotide or polydeoxribonucleotide, which may be unmodified RNA or DNA or modified RNA or DNA. Thus, for instance, polynucleotides as used herein refers to, among others, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded, or a mixture of single- and double-stranded regions. In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including inter alia, simple and complex cells. The term polynucleotide(s) embrace short polynucleotides often referred as oligonucleotides.

POLYPEPTIDES, as used herein, includes all polypeptides as described below. The basic structure of polypeptides is well known and has been described in innumerable textbooks and other publications in the art. In this context, the term is used herein to refer to any peptide or protein comprising two or more amino acids joined to each other in a linear chain by peptide bonds. As used herein, the term refers to both short chains, which also commonly are referred to in the art as peptides, oligopeptides and oligomers, for example, and to longer chains, which generally are referred to in the art as proteins, of which there are many types. It will be appreciated that polypeptides often contain amino acids other than the 20 amino acids commonly referred to as the 20 naturally occurring amino acids, and that many amino acids, including the terminal amino acids, may be modified in a given polypeptide, either by natural processes, such as processing and other post-translational modifications, but also by chemical modification techniques which are well known to the art. Even the common modifications that occur naturally in polypeptides are too numerous to list exhaustively here, but they are well described in basic texts and in more detailed monographs, as well as in a voluminous research literature, and they are well known to those of skill in the art. Among the known modifications which may be present in polypeptides of the present are, to name an illustrative few, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Such modifications are well known to those of skill and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as, for instance *PROTEINS— STRUCTURE AND MOLECULAR PROPERTIES,* 2nd Ed., T. E. Creighton, W. H. Freeman and Company, New York (1993). Many detailed reviews are available on this subject, such as, for example, those provided by Wold, F., Posttranslational Protein Modifications: Perspectives and Prospects, pgs. 1–12 in *POSTTRANSLATIONAL COVALENT MODIFICATION OF PROTEINS,* B. C. Johnson, Ed., Academic Press, New York (1983); Seifter et al., *Meth. Enzymol.* 182:626–646 (1990) and Rattan et al., *Protein Synthesis: Posttranslational Modifications and Aging, Ann. N.Y. Acad. Sci.* 663:48–62 (1992). It will be appreciated, as is well known and as noted above, that polypeptides are not always entirely linear. For instance, polypeptides may be branched as a result of ubiquitination, and they may be circular, with or without branching, generally as a result of posttranslation events, including natural processing event and events brought about by human manipulation which do not occur naturally. Circular, branched and branched circular polypeptides may be synthesized by non-translation natural process and by entirely synthetic methods, as well. Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in *E. coli* or other cells, prior to proteolytic processing, almost invariably will be N-formylmethionine. During post-translational modification of the peptide, a methionine residue at the NH$_2$-terminus may be deleted. Accordingly, this invention contemplates the use of both the methionine-containing and the methionineless amino terminal variants of the protein of the invention. The modifications that occur in a polypeptide often will be a function of how it is made. For polypeptides made by expressing a cloned gene in a host, for instance, the nature and extent of the modifications in large part will be determined by the host cell posttranslational modification capacity and the modification signals present in the polypeptide amino acid sequence. For instance, as is well known, glycosylation often does not occur in bacterial hosts such as, for example, *E. coli*. Accordingly, when glycosylation is desired, a polypeptide should be expressed in a glycosylating host, generally a eukaryotic cell. Insect cells often carry out the same posttranslational glycosylations as do mammalian cells and, for this reason, insect cell expression systems have been developed to express efficiently mammalian proteins having native patterns of glycosylation. Similar considerations apply to other modifications. It will be appreciated that the same type of modification may be present in the same or varying degree at several sites in a given polypeptide. Also, a given polypeptide may contain many types of modifications. In general, as used herein, the term polypeptide encompasses all such modifications, particularly those that are present in polypeptides synthesized by expressing a polynucleotide in a host cell.

VARIANT(S) of polynucleotides or polypeptides, as the term is used herein, are polynucleotides or polypeptides that differ from a reference polynucleotide or polypeptide, respectively. Variants in this sense are described below and elsewhere in the present disclosure in greater detail. With reference to polynucleotides, generally, differences are limited such that the nucleotide sequences of the reference and the variant are closely similar overall and, in many regions, identical. As noted below, changes in the nucleotide sequence of the variant may be silent. That is, they may not alter the amino acids encoded by the polynucleotide. Where alterations are limited to silent changes of this type, a variant will encode a polypeptide with the same amino acid sequence as the reference. Also as noted below, changes in the nucleotide sequence of the variant may alter the amino acid sequence of a polypeptide encoded by the reference polynucleotide. Such nucleotide changes may result in amino acid substitutions, additions, deletions, fusions and truncations in the polypeptide encoded by the reference sequence, as discussed below. With reference to polypeptides generally, differences are limited so that the sequences of the reference and the variant are closely similar overall and, in many region, identical. A variant and reference polypeptide may differ in amino acid sequence by one or more substitutions, additions, deletions, fusions and truncations, which may be present in any combination.

DESCRIPTION OF THE INVENTION

The present invention relates to novel Topoisomerase III polypeptides and polynucleotides encoding same, among other things, as described in greater detail below. In particular, the invention relates to polypeptides and polynucleotides of a novel Topoisomerase III gene of *Streptococcus pneumoniae*, which is related by amino acid sequence homology to *Bacillus subtilis* topoisomerase I polypeptide. The invention relates especially to Streptococcal Topoisomerase III having the nucleotide and amino acid sequences set out in FIG. I (SEQ ID NO: 1) and FIG. 2 (SEQ ID NO: 2), and to the Topoisomerase III nucleotide and amino acid sequences of the DNA isolatable from Deposit No. NCIMB 40794, which is herein referred to as "the deposited organism" or as the "DNA of the deposited organism." It will be appreciated that the nucleotide and amino acid sequences set out in FIG. 1 (SEQ ID NO: 1) and FIG. 2 (SEQ ID NO: 2) were obtained by sequencing the DNA of the deposited organism. Hence, the sequence of the deposited clone is controlling as to any discrepancies between it (and the sequence it encodes) and the sequences of FIG. 1 (SEQ ID NO: 1) and FIG. 2 (SEQ ID NO: 2).

Polynucleotides

In accordance with one aspect of the present invention, there are provided isolated polynucleotides which encode the Streptococcal Topoisomerase III polypeptide having the deduced amino acid sequence of FIG. 2 (SEQ ID NO: 2).

Using the information provided herein, such as the polynucleotide sequence set out in FIG. 1 (SEQ ID NO: 1), a polynucleotide of the present invention encoding Topoisomerase III polypeptide may be obtained using standard cloning and screening procedures. To obtain the polynucleotide encoding the protein using the DNA sequence given in SEQ ID NO: 1 typically a library of clones of chromosomal DNA of *S. pneumoniae* 0100993 in *E. coli* or some other suitable host is probed with a radiolabelled oligonucleotide, preferably a 17 mer or longer, derived from the sequence of FIG. 1. Clones carrying DNA identical to that of the probe can then be distinguished using high stringency washes. By sequencing the individual clones thus identified with sequencing primers designed from the original sequence it is then possible to extend the sequence in both directions to determine the full gene sequence. Conveniently such sequencing is performed using denatured double stranded DNA prepared from a plasmid clone. Suitable techniques are described by Maniatis, T., Fritsch, E. F. and Sambrook, J. in MOLECULAR CLONING, A Laboratory Manual (2nd edition 1989 Cold Spring Harbor Laboratory. see Screening By Hybridization 1.90 and Sequencing Denatured Double-Stranded DNA Templates 13.70). Illustrative of the invention, the polynucleotide set out in FIG. 1 (SEQ ID NO: 1) was discovered in a DNA library derived from *Streptococcus pneumoniae* 0100993 as described in Example 1.

Topoisomerase III of the invention is structurally related to other proteins of the bacterial Topoisomerase III family, as shown by comparing the sequence encoding Topoisomerase III from the deposited clone with that of sequence reported in the literature. A preferred DNA sequence is set out in FIG. 1( SEQ ID NO: 1). It contains an open reading frame encoding a protein of about 147 amino acid residues. The protein exhibits greatest homology to *Bacillus subtilis* topoisomerase I protein among known proteins. Topoisomerase III of FIG. 2 (SEQ ID NO: 2) has about 25.2% identity and 42.2% similarity with the amino acid sequence of *Bacillus subtilis* topoisomerase I.

Polynucleotides of the present invention may be in the form of RNA, such as mRNA, or in the form of DNA, including, for instance, cDNA and genomic DNA obtained by cloning or produced by chemical synthetic techniques or by a combination thereof. The DNA may be double-stranded or single-stranded. Single-stranded DNA may be the coding strand, also known as the sense strand, or it may be the non-coding strand, also referred to as the anti-sense strand.

The coding sequence which encodes the polypeptide may be identical to the coding sequence of the polynucleotide shown in FIG. 1 (SEQ ID NO: 1). It also may be a polynucleotide with a different sequence, which, as a result of the redundancy (degeneracy) of the genetic code, encodes the polypeptide of FIG. 2 (SEQ ID NO: 2).

Polynucleotides of the present invention which encode the polypeptide of FIG. 2 (SEQ ID NO: 2) may include, but are not limited to the coding sequence for the mature polypeptide, by itself; the coding sequence for the mature polypeptide and additional coding sequences, such as those encoding a leader or secretory sequence, such as a pre-, or pro- or prepro- protein sequence; the coding sequence of the mature polypeptide, with or without the aforementioned additional coding sequences, together with additional, non-coding sequences, including for example, but not limited to non-coding 5' and 3' sequences, such as the transcribed, non-translated sequences that play a role in transcription (including termination signals, for example), ribosome binding, mRNA stability elements, and additional coding sequence which encode additional amino acids, such as those which provide additional functionalities. The DNA may also comprise a promoter region which functions to direct the transcription of the mRNA encoding the Topoisomerase III of this invention. Such promoter may be independently useful to direct the transcription of heterologous gene in recombinant expression system. Furthermore, the polypeptide may be fused to a marker sequence, such as a peptide, which facilitates purification of the fused polypeptide. In certain embodiments of this aspect of the invention, the marker sequence is a hexa-histidine peptide, such as the tag provided in the pQE vector (Qiagen, Inc.), among others, many of which are commercially available. As described in Gentz et al., *Proc. Nat'l. Acad. Sci.. USA* 86:821–824 (1989), for instance, hexa-histidine provides for convenient purification of the fusion protein. The HA tag may also be used to create fusion proteins and corresponds to an epitope derived of influenza hemagglutinin protein, which has been described by Wilson et al., *Cell* 37:767 (1984), for instance.

In accordance with the foregoing, the term "polynucleotide encoding a polypeptide" as used herein encompasses polynucleotides which include a sequence encoding a polypeptide of the present invention, particularly bacterial, and more particularly *Streptococcus pneumoniae* Topoisomerase III having the amino acid sequence set out in FIG. 2 (SEQ ID NO: 2). The term encompasses polynucleotides that include a single continuous region or discontinuous regions encoding the polypeptide (for example, interrupted by integrated phage or insertion sequence or editing) together with additional regions, that also may contain coding and/or non-coding sequences.

The present invention further relates to variants of the herein above described polynucleotides which encode for fragments, analogs and derivatives of the polypeptide having the deduced amino acid sequence of FIG. 2 (SEQ ID NO: 2). A variant of the polynucleotide may be a naturally occurring variant such as a naturally occurring allelic variant, or it may be a variant that is not known to occur naturally. Such non-naturally occurring variants of the polynucleotide may be made by mutagenesis techniques, including those applied to polynucleotides, cells or organisms.

Among variants in this regard are variants that differ from the aforementioned polynucleotides by nucleotide substitutions, deletions or additions. The substitutions may involve one or more nucleotides. The variants may be altered in coding or non-coding regions or both. Alterations in the coding regions may produce conservative or non-conservative amino acid substitutions, deletions or additions.

Among the particularly preferred embodiments of the invention in this regard are polynucleotides encoding polypeptides having the amino acid sequence of Streptococcal Topoisomerase III set out in FIG. 2 (SEQ ID NO: 2); variants, analogs, derivatives and fragments thereof.

Further particularly preferred in this regard are polynucleotides encoding Topoisomerase III variants, analogs, derivatives and fragments, and variants, analogs and derivatives of the fragments, which have the amino acid sequence of Streptococcal Topoisomerase III polypeptide of FIG. 2 (SEQ ID NO: 2) in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of Topoisomerase III. Also especially preferred in this regard are conservative substitutions. Most highly preferred are polynucleotides encoding polypeptides having the amino acid sequence of FIG. 2 (SEQ ID NO: 2), without substitutions.

Further preferred embodiments of the invention are polynucleotides that are at least 70% identical to a polynucleotide encoding Topoisomerase III polypeptide having the amino acid sequence set out in FIG. 2 (SEQ ID NO: 2), and polynucleotides which are complementary to such polynucleotides. Alternatively, most highly preferred are polynucleotides that comprise a region that is at least 80% identical to a polynucleotide encoding Topoisomerase III polypeptide of the *Streptococcus pneumoniae* DNA of the deposited clone and polynucleotides complementary thereto. In this regard, polynucleotides at least 90% identical to the same are particularly preferred, and among these particularly preferred polynucleotides, those with at least 95% are especially preferred. Furthermore, those with at least 97% are highly preferred among those with at least 95%, and among these those with at least 98% and at least 99% are particularly highly preferred, with at least 99% being the more preferred.

Particularly preferred embodiments in this respect, moreover, are polynucleotides which encode polypeptides which retain substantially the same biological function or activity as the mature polypeptide encoded by the DNA of FIG. 1 (SEQ ID NO: 1).

The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 95% and preferably at least 97% identity between the sequences.

As discussed additionally herein regarding polynucleotide assays of the invention, for instance, polynucleotides of the invention as discussed above, may be used as a hybridization probe for RNA, cDNA and genomic DNA to isolate full-length cDNAs and genomic clones encoding Topoisomerase III and to isolate cDNA and genomic clones of other genes that have a high sequence similarity to the Topoisomerase III gene. Such probes generally will comprise at least 15 bases. Preferably, such probes will have at least 30 bases and may have at least 50 bases. Particularly preferred probes will have at least 30 bases and will have 50 bases or less.

For example, the coding region of the Topoisomerase III gene may be isolated by screening using the known DNA sequence to synthesize an oligonucleotide probe. A labeled oligonucleotide having a sequence complementary to that of a gene of the present invention is then used to screen a library of cDNA, genomic DNA or mRNA to determine which members of the library to which the probe hybridizes.

The polynucleotides and polypeptides of the present invention may be employed as research reagents and materials for discovery of treatments of and diagnostics for disease, particularly human disease, as further discussed herein relating to polynucleotide assays.

The polynucleotides of the invention that are oligonucleotides, derived from the sequences (SEQ ID NO: 1) may be used as PCR primers in the process herein described to determine whether or not the *Streptococcus pneumoniae* genes identified herein in whole or in part are transcribed in infected tissue. It is recognized that such sequences will also have utility in diagnosis of the stage of infection and type of infection the pathogen has attained.

The polynucleotides may encode a polypeptide which is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may allow protein transport, may lengthen or shorten protein half-life or may facilitate manipulation of a protein for assay or production, among other things. As generally is the case, in vivo, the additional amino acids may be processed away from the mature protein by cellular enzymes.

A precursor protein, having the mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

In sum, a polynucleotide of the present invention may encode a mature protein, a mature protein plus a leader sequence (which may be referred to as a preprotein), a precursor of a mature protein having one or more prosequences which are not the leader sequences of a preprotein, or a preproprotein, which is a precursor to a proprotein, having a leader sequence and one or more prosequences, which generally are removed during processing steps that produce active and mature forms of the polypeptide.

Deposited Materials

*Streptococcus pneumoniae* 0100993 was deposited at the National Collection of Industrial and Marine Bacteria Ltd. (NCIMB), Aberdeen, Scotland under number NCIMB 40794 on Apr. 11, 1996.

The deposit has been made under the terms of the Budapest Treaty on the International Recognition of the Deposit of Micro-organisms for Purposes of Patent Procedure. The strain will be irrevocably and without restriction or condition released to the public upon the issuance of a patent. The deposit is provided merely as convenience to those of skill in the art and is not an admission that a deposit is required for enablement, such as that required under 35 U.S.C. §112.

The sequence of the polynucleotides contained in the deposited material, as well as the amino acid sequence of the polypeptide encoded thereby, are controlling in the event of any conflict with any description of sequences herein.

A license may be required to make, use or sell the deposited materials, and no such license is hereby granted.

Polypeptides

The present invention further relates to a bacterial Topoisomerase III polypeptide that has the deduced amino acid sequence of FIG. 2 (SEQ ID NO: 2).

The invention also relates to fragments, analogs and derivatives of these polypeptides. The terms "fragment," "derivative" and "analog" when referring to the polypeptide of FIG. 2 (SEQ ID NO: 2), means a polypeptide which retains essentially the same biological function or activity as such polypeptide. Fragments derivatives and analogs that retain at least 90% of the activity of the native Topoisomerase III are preferred. Fragments derivatives and analogs that retain at least 95% of the activity of the native Topoisomerase III are preferred Thus, an analog includes a proprotein which can be activated by cleavage of the proprotein portion to produce an active mature polypeptide.

The polypeptide of the present invention may be a recombinant polypeptide, a natural polypeptide or a synthetic polypeptide. In certain preferred embodiments it is a recombinant polypeptide.

The fragment, derivative or analog of the polypeptide of FIG. 2 (SEQ ID NO: 2) may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be obtained by those of ordinary skill in the art, from the teachings herein.

Among the particularly preferred embodiments of the invention in this regard are polypeptides having the amino acid sequence of Streptococcal Topoisomerase III set out in FIG. 2 (SEQ ID NO: 2), variants, analogs, derivatives and fragments thereof, and variants, analogs and derivatives of the fragments.

Among preferred variants are those that vary from a reference by conservative amino acid substitutions. Such substitutions are those that substitute a given amino acid in a polypeptide by another amino acid of like characteristics. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Further particularly preferred in this regard are variants, analogs, derivatives and fragments, and variants, analogs and derivatives of the fragments, having the amino acid sequence of the Topoisomerase III polypeptide of FIG. 2 (SEQ ID NO: 2), in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of the Topoisomerase III. Also especially preferred in this regard are conservative substitutions. Most highly preferred are polypeptides having the amino acid sequence of FIG. 2 (SEQ ID NO: 2) without substitutions.

The polypeptides and polynucleotides of the present invention are preferably provided in an isolated form, and preferably are purified to homogeneity.

The polypeptides of the present invention include the polypeptide of FIG. 2 (SEQ ID NO: 2), in particular the mature polypeptide as well as polypeptides which have at least 80% identity to the polypeptide of FIG. 2 (SEQ ID NO: 2) and preferably at least 90% similarity (more preferably at least 90% identity) to the polypeptide of FIG. 2 (SEQ ID NO: 2) and more preferably at least 95% similarity; and still more preferably at least 95% identity to the polypeptide of FIG. 2 (SEQ ID NO: 2) and also include portions of such polypeptides with such portion of the polypeptide generally containing at least 30 contiguous amino acids and more preferably at least 50 contiguous amino acids.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

Fragments

Also among preferred embodiments of this aspect of the present invention are polypeptides comprising fragments of Topoisomerase III, most particularly fragments of Topoisomerase III having the amino acid set out in FIG. 2 (SEQ ID NO: 2), and fragments of variants and derivatives of the Topoisomerase III of FIG. 2 (SEQ ID NO: 2).

In this regard a fragment is a polypeptide having an amino acid sequence that entirely is the same as part but not all of the amino acid sequence of the aforementioned Topoisomerase III polypeptides and variants or derivatives thereof.

Such fragments may be "free-standing," i.e., not part of or fused to other amino acids or polypeptides, or they may be comprised within a larger polypeptide of which they form a part or region. When comprised within a larger polypeptide, the presently discussed fragments most preferably form a single continuous region. However, several fragments may be comprised within a single larger polypeptide. For instance, certain preferred embodiments relate to a fragment of a Topoisomerase III polypeptide of the present comprised within a precursor polypeptide designed for expression in a host and having heterologous pre and pro-polypeptide regions fused to the amino terminus of the Topoisomerase III fragment and an additional region fused to the carboxyl terminus of the fragment. Therefore, fragments in one aspect of the meaning intended herein, refers to the portion or portions of a fusion polypeptide or fusion protein derived from Topoisomerase III.

Representative examples of polypeptide fragments of the invention, include, for example, may be mentioned those which have from about 5–15, 10–20, 15–40, 30–55, 41–75, 41–80, 41–90, 50–100, 75–100, 90–115, 100–125, and 110–140 amino acids long.

In this context about includes the particularly recited range and ranges larger or smaller by several, a few, 5, 4, 3, 2 or 1 amino acid at either extreme or at both extremes.

Among especially preferred fragments of the invention are truncation mutants of Topoisomerase III. Truncation mutants include Topoisomerase III polypeptides having the amino acid sequence of FIG. 2 (SEQ ID NO: 2), or of variants or derivatives thereof, except for deletion of a continuous series of residues (that is, a continuous region, part or portion) that includes the amino terminus, or a continuous series of residues that includes the carboxyl terminus or, as in double truncation mutants, deletion of two continuous series of residues, one including the amino terminus and one including the carboxyl terminus. Fragments having the size ranges set out above also are preferred embodiments of truncation fragments, which are especially preferred among fragments generally. Degradation forms of the polypeptides of the invention in a host cell are also preferred.

Also preferred in this aspect of the invention are fragments characterized by structural or functional attributes of Topoisomerase III. Preferred embodiments of the invention in this regard include fragments that comprise alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of Topoisomerase III.

Further preferred regions are those that mediate activities of Topoisomerase III. Most highly preferred in this regard are fragments that have a chemical, biological or other activity of Topoisomerase III, including those with a similar activity or an improved activity, or with a decreased undesirable activity. Routinely one generates the fragment by well-known methods then compares the activity of the fragment to nature Topoisomerase I in a convenient assay such as listed hereinbelow. Highly preferred in this regard are fragments that contain regions that are homologs in sequence, or in position, or in both sequence and to active regions of related polypeptides, such as the related polypeptides set out in FIG. 2 (SEQ ID NO: 2), which include *Bacillus subtilis* topoisomerase I. Among particularly preferred fragments in these regards are truncation mutants, as discussed above. Further preferred polynucleotide fragments are those that are antigenic or immunogenic in an animal, especially in a human.

It will be appreciated that the invention also relates to, among others, polynucleotides encoding the aforementioned fragments, polynucleotides that hybridize to polynucleotides encoding the fragments, particularly those that hybridize under stringent conditions, and polynucleotides, such as PCR primers, for amplifying polynucleotides that encode the fragments. In these regards, preferred polynucleotides are those that correspondent to the preferred fragments, as discussed above.

Vectors, Host Cells, Expression

The present invention also relates to vectors which comprise a polynucleotide or polynucleotides of the present invention, host cells which are genetically engineered with vectors of the invention and the production of polypeptides of the invention by recombinant techniques.

Host cells can be genetically engineered to incorporate polynucleotides and express polypeptides of the present invention. Introduction of a polynucleotides into the host cell can be affected by calcium phosphate transfection, DEAE-dextran mediated transfection, transvection, microinjection, cationic lipid-mediated transfection, electroporation, transduction, scrape loading, ballistic introduction, infection or other methods. Such methods are described in many standard laboratory manuals, such as Davis et al., *BASIC METHODS IN MOLECULAR BIOLOGY*, (1986) and Sambrook et al., *MOLECULAR CLONING: A LABORATORY MANUAL,* 2nd Ed., Cold Spring Harbor Laboratory Press, Cold Spring Harbor, N.Y. (1989).

Polynucleotide constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., MOLECULAR CLONING: A LABORATORY MANUAL, 2nd Ed., Cold Spring Harbor Laboratory Press, Cold Spring Harbor, N.Y. (1989).

In accordance with this aspect of the invention the vector may be, for example, a plasmid vector, a single or double-stranded phage vector, a single or double-stranded RNA or DNA viral vector. Plasmids generally are designated herein by a lower case p preceded and/or followed by capital letters and/or numbers, in accordance with standard naming conventions that are familiar to those of skill in the art. Starting plasmids disclosed herein are either commercially available, publicly available, or can be constructed from available plasmids by routine application of well known, published procedures. Many plasmids and other cloning and expression vectors that can be used in accordance with the present invention are well known and readily available to those of skill in the art.

Preferred among vectors, in certain respects, are those for expression of polynucleotides and polypeptides of the present invention. Generally, such vectors comprise cis-acting control regions effective for expression in a host operatively linked to the polynucleotide to be expressed. Appropriate trans-acting factors either are supplied by the host, supplied by a complementing vector or supplied by the vector itself upon introduction into the host.

In certain preferred embodiments in this regard, the vectors provide for specific expression. Such specific expression may be inducible expression or expression only in certain types of cells or both inducible and cell-specific. Particularly preferred among inducible vectors are vectors that can be induced for expression by environmental factors that are easy to manipulate, such as temperature and nutrient additives. A variety of vectors suitable to this aspect of the invention, including constitutive and inducible expression vectors for use in prokaryotic and eukaryotic hosts, are well known and employed routinely by those of skill in the art.

A great variety of expression vectors can be used to express a polypeptide of the invention. Such vectors include, among others, chromosomal, episomal and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids, all may be used for expression in accordance with this aspect of the present invention. Generally, any vector suitable to maintain, propagate or express polynucleotides to express a polypeptide in a host may be used for expression in this regard.

The appropriate DNA sequence may be inserted into the vector by any of a variety of well-known and routine techniques, such as, for example, those set forth in Sambrook et al., MOLECULAR CLONING, A LABORATORY MANUAL, 2nd Ed.; Cold Spring Harbor Laboratory Press, Cold Spring Harbor, N.Y. (1989).

The DNA sequence in the expression vector is operatively linked to appropriate expression control sequence(s), including, for instance, a promoter to direct mRNA transcription. Representatives of such promoters include, but are not limited to, the phage lambda PL promoter, the E. coli lac, tip and tac promoters, the SV40 early and late promoters and promoters of retroviral LTRs.

In general, expression constructs will contain sites for transcription initiation and termination, and, in the transcribed region, a ribosome binding site for translation. The coding portion of the mature transcripts expressed by the constructs will include a translation initiating AUG at the beginning and a termination codon appropriately positioned at the end of the polypeptide to be translated.

In addition, the constructs may contain control regions that regulate as well as engender expression. Generally, in accordance with many commonly practiced procedures, such regions will operate by controlling transcription, such as transcription factors, repressor binding sites and termination, among others.

Vectors for propagation and expression generally will include selectable markers and amplification regions, such as, for example, those set forth in Sambrook et al., MOLECULAR CLONING, A LABORATORY MANUAL, 2nd Ed.; Cold Spring Harbor Laboratory Press, Cold Spring Harbor, N.Y. (1989).

Representative examples of appropriate hosts include bacterial cells, such as streptococci, Streptococci, E. coli, streptomyces and Bacillus subtilis cells; fungal cells, such as yeast cells and Aspergillus cells; insect cells such as Drosophila S2 and Spodoptera Sf9 cells; animal cells such as CHO, COS, HeLa, C127, 3T3, BHK, 293 and Bowes melanoma cells; and plant cells.

The following vectors, which are commercially available, are provided by way of example. Among vectors preferred for use in bacteria are pQE70, pQE60 and pQE-9, available from Qiagen; pBS vectors, Phagescript vectors, Bluescript vectors, pNH8A, pNH16a, pNH 18A, pNH46A, available from Stratagene; and ptrc99a, pKK223-3, pKK233-3, pDR540, pRIT5 available from Pharmacia, and pBR322 (ATCC 37017). Among preferred eukaryotic vectors are pWLNEO, pSV2CAT, pOG44, pXT1 and pSG available from Stratagene; and pSVK3, pBPV, pMSG and pSVL available from Pharmacia. These vectors are listed solely by way of illustration of the many commercially available and well known vectors that are available to those of skill in the art for use in accordance with this aspect of the present invention. It will be appreciated that any other plasmid or vector suitable for, for example, introduction, maintenance, propagation or expression of a polynucleotide or polypeptide of the invention in a host may be used in this aspect of the invention.

Promoter regions can be selected from any desired gene using vectors that contain a reporter transcription unit lacking a promoter region, such as a chloramphenicol acetyl transferase ("CAT") transcription unit, downstream of restriction site or sites for introducing a candidate promoter fragment; i.e., a fragment that may contain a promoter. As is well known, introduction into the vector of a promoter-containing fragment at the restriction site upstream of the cat gene engenders production of CAT activity, which can be detected by standard CAT assays. Vectors suitable to this end are well known and readily available, such as pKK232-8 and pCM7. Promoters for expression of polynucleotides of the present invention include not only well known and readily available promoters, but also promoters that readily may be obtained by the foregoing technique, using a reporter gene.

Among known prokaryotic promoters suitable for expression of polynucleotides and polypeptides in accordance with the present invention are the *E. coli* lacI and lacZ and promoters, the T3 and T7 promoters, the gpt promoter, the lambda PR, PL promoters and the trp promoter.

Among known eukaryotic promoters suitable in this regard are the CMV immediate early promoter, the HSV thymidine kinase promoter, the early and late SV40 promoters, the promoters of retroviral LTRs, such as those of the Rous sarcoma virus ("RSV"), and metallothionein promoters, such as the mouse metallothionein-I promoter.

Recombinant expression vectors will include, for example, origins of replication, a promoter preferably derived from a highly-expressed gene to direct transcription of a downstream structural sequence, and a selectable marker to permit isolation of vector containing cells after exposure to the vector.

Polynucleotides of the invention, encoding the heterologous structural sequence of a polypeptide of the invention generally will be inserted into the vector using standard techniques so that it is operably linked to the promoter for expression. The polynucleotide will be positioned so that the transcription start site is located appropriately 5' to a ribosome binding site. The ribosome binding site will be 5' to the AUG that initiates translation of the polypeptide to be expressed. Generally, there will be no other open reading frames that begin with an initiation codon, usually AUG, and lie between the ribosome binding site and the initiation codon. Also, generally, there will be a translation stop codon at the end of the polypeptide and there will be a polyadenylation signal in constructs for use in eukaryotic hosts. Transcription termination signal appropriately disposed at the 3' end of the transcribed region may also be included in the polynucleotide construct.

For secretion of the translated protein into the lumen of the endoplasmic reticulum, into the periplasmic space or into the extracellular environment, appropriate secretion signals may be incorporated into the expressed polypeptide. These signals may be endogenous to the polypeptide or they may be heterologous signals.

The polypeptide may be expressed in a modified form, such as a fusion protein, and may include not only secretion signals but also additional heterologous functional regions. Thus, for instance, a region of additional amino acids, particularly charged amino acids, may be added to the N- or C-terminus of the polypeptide to improve stability and persistence in the host cell, during purification or during subsequent handling and storage. Also, region also may be added to the polypeptide to facilitate purification. Such regions may be removed prior to final preparation of the polypeptide. The addition of peptide moieties to polypeptides to engender secretion or excretion, to improve stability or to facilitate purification, among others, are familiar and routine techniques in the art. A preferred fusion protein comprises a heterologous region from immunoglobulin that is useful to solubilize or purify polypeptides. For example, EP-A-O 464 533 (Canadian counterpart 2045869) discloses fusion proteins comprising various portions of constant region of immunoglobulin molecules together with another protein or part thereof. In drug discovery, for example, proteins have been fused with antibody Fc portions for the purpose of high-throughput screening assays to identify antagonists. See, D. Bennett et al., Journal of Molecular Recognition, 8:52–58 (1995) and K. Johanson et al., The Journal of Biological Chemistry, 270, (16):9459–9471 (1995).

Cells typically then are harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Mammalian expression vectors may comprise an origin of replication, a suitable promoter and enhancer, and also any necessary ribosome binding sites, polyadenylation sites, splice donor and acceptor sites, transcriptional termination sequences, and 5' flanking non-transcribed sequences that are necessary for expression. In certain preferred embodiments in this regard DNA sequences derived from the SV40 splice sites, and the SV40 polyadenylation sites are used for required non-transcribed genetic elements of these types.

Topoisomerase III polypeptide can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Well known techniques for refolding protein may be employed to regenerate active conformation when the polypeptide is denatured during isolation and or purification.

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

Topoisomerase III polynucleotides and polypeptides may be used in accordance with the present invention for a variety of applications, particularly those that make use of the chemical and biological properties of Topoisomerase III. Additional applications relate to diagnosis and to treatment of disorders of cells, tissues and organisms. These aspects of the invention are illustrated further by the following discussion.

Polynucleotide Assays

This invention is also related to the use of the Topoisomerase III polynucleotides to detect complementary polynucleotides such as, for example, as a diagnostic reagent. Detection of a bacterial Topoisomerase III in a eukaryote, particularly a mammal, and especially a human, will provide a diagnostic method that can add to, define or allow a diagnosis of a disease. Eukaryotes (herein also "individual (s)"), particularly mammals, and especially humans, infected by a Topoisomerase III producing bacterium may be detected at the DNA or RNA level by a variety of techniques. Nucleic acids for diagnosis may be obtained from an individual's cells and tissues, such as bone, blood, muscle, cartilage, and skin. Tissue biopsy and autopsy material is also preferred for samples from an individual to use in a diagnostic assay. The bacterial DNA may be used directly for detection or may be amplified enzymatically by using PCR prior to analysis. PCR (Saiki et al., *Nature* 324:163–166 (1986)). RNA or cDNA may also be used in the same ways. As an example, PCR primers complementary to the nucleic acid encoding Topoisomerase III can be used to identify and analyze Topoisomerase III presence and expression. Using PCR, characterization of the strain of prokaryote present in a eukaryote, particularly a mammal, and especially a human, may be made by an analysis of the genotype of the prokaryote gene. For example, deletions and insertions can be detected by a change in size of the amplified product in comparison to the genotype of a reference sequence. Point mutations can be identified by hybridizing amplified DNA to radiolabeled Topoisomerase III RNA or alternatively, radiolabeled Topoisomerase III antisense DNA sequences. Perfectly matched sequences can be distinguished from mismatched duplexes by RNase A digestion or by differences in melting temperatures.

Sequence differences between a reference gene and genes having mutations also may be revealed by direct DNA sequencing. In addition, cloned DNA segments may be employed as probes to detect specific DNA segments. The sensitivity of such methods can be greatly enhanced by appropriate use of PCR or another amplification method. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic typing of various strains of bacteria based on DNA sequence differences may be achieved by detection of alteration in electrophoretic mobility of DNA fragments in gels, with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., *Science,* 230:1242 (1985)).

Sequence changes at specific locations also may be revealed by nuclease protection assays, such as RNase and S1 protection or the chemical cleavage method (e.g., Cotton et al., *Proc. Nat'l. Acad. Sci.. USA,* 85:4397–4401 (1985)).

Thus, the detection of a specific DNA sequence may be achieved by methods such as hybridization, RNase protection, chemical cleavage, direct DNA sequencing or the use of restriction enzymes, (e.g., restriction fragment length polymorphisms ("RFLP") and Southern blotting of genomic DNA.

In addition to more conventional gel-electrophoresis and DNA sequencing, mutations also can be detected by in situ analysis.

Cells carrying mutations or polymorphisms in the gene of the present invention may also be detected at the DNA level by a variety of techniques, to allow for serotyping, for example. Nucleic acids for diagnosis may be obtained from an infected individual's cells, including but not limited to blood, urine, saliva, tissue biopsy and autopsy material or from bacteria isolated and cultutered from the above sources. The bacterial DNA may be used directly for detection or may be amplified enzymatically by using PCR (Saiki et al, Nature, 324:163–166 (1986)) prior to analysis. RT-PCR can also be used to detect mutations. It is particularly preferred to used RT-PCR in conjunction with automated detection systems, such as, for example, GeneScan. RNA or cDNA may also be used for the same purpose, PCR or RT-PCR. As an example, PCR primers complementary to the nucleic acid encoding Topoisomerase III can be made using known methods and used to identify and analyze mutations. For example, deletions and insertions can be detected by a change in size of the amplified product in comparison to the normal genotype. Point mutations can be identified by hybridizing amplified DNA to radiolabeled RNA or alternatively, radiolabeled antisense DNA sequences. Perfectly matched sequences can be distinguished from mismatched duplexes by RNase A digestion or by differences in melting temperatures. These primers may be used for amplifying Topoisomerase III cDNA isolated from a sample derived from an individual. The invention also provides such primers with 1, 2, 3 or 4 nucleotides removed from the 5' and/or the 3' end. The primers may be used to amplify the gene isolated from the individual such that the gene may then be subject to various techniques for elucidation of the DNA sequence. In this way, mutations in the DNA sequence may be detected.

Polypeptide Assays

The present invention also relates to a diagnostic assays such as quantitative and diagnostic assays for detecting levels of Topoisomerase III protein in cells and tissues, including determination of normal and abnormal levels. Thus, for instance, a diagnostic assay in accordance with the invention for detecting expression of Topoisomerase III protein compared to normal control tissue samples may be used to detect the presence of an infection. Assay techniques that can be used to determine levels of a protein, such as an Topoisomerase III protein of the present invention, in a sample derived from a host are well-known to those of skill in the art. Such assay methods include radioimmunoassays, competitive-binding assays, Western Blot analysis and ELISA assays. Among these ELISAs frequently are preferred. An ELISA assay initially comprises preparing an antibody specific to Topoisomerase III, preferably a monoclonal antibody. In addition a reporter antibody generally is prepared which binds to the monoclonal antibody. The reporter antibody is attached a detectable reagent such as radioactive, fluorescent or enzymatic reagent, in this example horseradish peroxidase enzyme.

Antibodies

The polypeptides, their fragments or other derivatives, or analogs thereof, or cells expressing them can be used as an immunogen to produce antibodies thereto. The present invention includes, for examples monoclonal and polyclonal antibodies, chimeric, single chain, and humanized antibodies, as well as Fab fragments, or the product of an Fab expression library.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique known in the art which provides antibodies produced by continuous cell line cultures can be used. Examples include various techniques, such as those in Kohler, G. and Milstein, C., *Nature* 256:495–497 (1975); Kozbor et al., *Immunology Today* 4:72 (1983); Cole et al., pg. 77–96 in *MONOCLONAL ANTIBODIES AND CANCER THERAPY,* Alan R. Liss, Inc. (1985).

Techniques described for the production of single chain antibodies (U.S. Pat. No. 4,946,778) can be adapted to produce single chain antibodies to immunogenic polypeptide products of this invention. Also, transgenic mice, or other organisms such as other mammals, may be used to express humanized antibodies to immunogenic polypeptide products of this invention.

Alternatively phage display technology could be utilized to select antibody genes with binding activities towards the polypeptide either from repertoires of PCR amplified v-genes of lymphocytes from humans screened for possessing anti-Fbp or from naive libraries (McCafferty, J. et al., Nature 348, 552–554 (1990); Marks, J. et al., Biotechnology 10: 779–783 (1992). The affinity of these antibodies can also be improved by chain shuffling (Clackson, T. et al., Nature 352, 624–628 (1991).

If two antigen binding domains are present each domain may be directed against a different epitope—termed 'bispecific' antibodies.

The above-described antibodies may be employed to isolate or to identify clones expressing the polypeptide or purify the polypeptide of the present invention by attachment of the antibody to a solid support for isolation and/or purification by affinity chromatography.

Thus among others, antibodies against Topoisomerase III may be employed to inhibit and/or treat infections, particularly bacterial infections, and especially Streptococcal infections as well as to monitor the effectiveness of antibiotic treatment.

Polypeptide derivatives include antigenically, epitopically or immunologically equivalent derivatives which form a particular aspect of this invention. The term "antigenically equivalent derivative" as used herein encompasses a polypeptide or its equivalent which will be specifically recognized by certain antibodies which, when raised to the protein or polypeptide according to the present invention, interfere with the immediate physical interaction between pathogen and mammalian host. The term "immunologically equivalent derivative" as used herein encompasses a peptide or its equivalent which when used in a suitable formulation to raise antibodies in a vertebrate, the antibodies act to interfere with the immediate physical interaction between pathogen and mammalian host.

The polypeptide, such as an antigenically or immunologically equivalent derivative or a fusion protein thereof is used as an antigen to immunize a mouse or other animal such as a rat or chicken. The fusion protein may provide stability to the polypeptide. The antigen may be associated, for example by conjugation, with an immunogenic carrier protein for example bovine serum albumin (BSA) or keyhole limpet haemocyanin (KLH). Alternatively a multiple antigenic peptide comprising multiple copies of the protein or polypeptide, or an antigenically or immunologically equivalent polypeptide thereof may be sufficiently antigenic to improve immunogenicity so as to obviate the use of a carrier.

Preferably the antibody or derivative thereof is modified to make it less immunogenic in the individual. For example, if the individual is human the antibody may most preferably be "humanised"; where the complimentarity determining region(s) of the hybridoma-derived antibody has been transplanted into a human monoclonal antibody, for example as described in Jones, P. et al. Nature 321:522–525 (1986)or Tempest et al., Biotechnology 9:266–273 (1991).

The use of a polynucleotide of the invention in genetic immunization will preferably employ a suitable delivery method such as direct injection of plasmid DNA into muscles (Wolff et al., Hum Mol Genet 1:363 (1992), Manthorpe et al., Hum. Gene Ther. 1963:4:419 (1963), delivery of DNA complexed with specific protein carriers (Wu et al, J. Biol. Chem. 264:16985 (1989), coprecipitation of DNA with calcium phosphate (Benvenisty and Reshef, Proc. Nat'l Acad. Sci. (USA),:83;9551 (1986), encapsulation of DNA in various forms of liposomes (Kaneda et al., Science 243:375 (1989), particle bombardment (Tang et al, Nature, (1992) 356:152, Eisenbraun et al. DNA Cell Biol 12:791(1993) and in vivo infection using cloned retroviral vectors (Seeger et al., Proc. Nat'l Acad. Sci. (USA) 81:5849 (1984).

Topoisomerase III Binding Molecules and Assays

This invention also provides a method for identification of molecules, such as binding molecules, that bind Topoisomerase III. Genes encoding proteins that bind Topoisomerase III, such as binding proteins, can be identified by numerous methods known to those of skill in the art, for example, ligand panning and FACS sorting. Such methods are described in many laboratory manuals such as, for instance, Coligan et al., Current Protocols in Immunology 1(2): Chapter 5 (1991).

For instance, expression cloning may be employed for this purpose. To this end polyadenylated RNA is prepared from a cell expressing Topoisomerase III, a cDNA library is created from this RNA, the library is divided into pools and the pools are transfected individually into cells that are not expressing to Topoisomerase III. The transfected cells then are exposed to labeled Topoisomerase III. Topoisomerase III can be labeled by a variety of well-known techniques including standard methods of radio-iodination or inclusion of a recognition site for a site-specific protein kinase.) Following exposure, the cells are fixed and binding of Topoisomerase III is determined. These procedures conveniently are carried out on glass slides.

Pools are identified of cDNA that produced Topoisomerase III-binding cells. Sub-pools are prepared from these positives, transfected into host cells and screened as described above. Using an iterative sub-pooling and re-screening process, one or more single clones that encode the putative binding molecule, such as a binding molecule, can be isolated.

Alternatively a labeled ligand can be photoaffinity linked to a cell extract, such as a membrane or a membrane extract, prepared from cells that express a molecule that it binds, such as a binding molecule. Cross-linked material is resolved by polyacrylamide gel electrophoresis ("PAGE") and exposed to X-ray film. The labeled complex containing the ligand-binding can be excised, resolved into peptide fragments, and subjected to protein microsequencing. The amino acid sequence obtained from microsequencing can be used to design unique or degenerate oligonucleotide probes to screen cDNA libraries to identify genes encoding the putative binding molecule.

Polypeptides of the invention also can be used to assess Topoisomerase III binding capacity of Topoisomerase III binding molecules, such as binding molecules, in cells or in cell-free preparations.

Polypeptides of the invention may also be used to assess the binding or small molecule substrates and ligands in, for example, cells, cell-free preparations, chemical libraries, and natural product mixtures. These substrates and ligands may be natural substrates and ligands or may be structural or functional mimetics.

Antagonists and Agonists-Assays and Molecules

As mentioned above, both increases and decreases in DNA density have been associated with bacterial responses to environmental challenges. Accordingly, modulating, i.e., agonizing or antagonizing, the appropriate response could result in a potential antibiotic effect.

The invention also provides a method of screening compounds to identify those which enhance or block the action of Topoisomerase III on cells, such as its interaction with substrate molecules, such as supercoiled DNA. Compounds which block the action of Topoisomerase III on cells include those which act as poisons and stabilize Topoisomerase III in a covalent complex with DNA, resulting in an inhibitory effect on cell growth. An antagonist is a compound which decreases the natural biological functions of Topoisomerase III. An agonist is a compound which increases the natural biological functions of Topoisomerase III.

Barrett et al., *Antimicrob. Agents Chemother.* 34:1 (1990) review in-vitro assays which can be used to measure inhibition of topoisomerases. These assays can be categorized as catalytic assays and noncatalytic assays. Catalytic assays for bacterial topoisomerase III include, for example, assays to measure the relaxation of supercoiled DNA. Noncatalytic assays, also known as 'cleavable complex' assays, measure the formation of a key covalent reaction intermediate. Froelich-Ammon and Osheroff *J. Biol. Chem.* 270:21429 (1995) review the mechanistic basis of noncatalytic assays of topoisomerase poisons.

Supercoiled DNA Relaxation Assay

To screen for inhibitors of the relaxation reaction, a candidate inhibitor and a preparation of Topoisomerase III are incubated with a supercoiled DNA substrate, for example plasmid or phage DNA, in an appropriate buffer containing $Mg^{2+}$, or an alternative divalent metal ion. Reaction products are separated by agarose gel electrophoresis, visualized by ethidium bromide staining, and quantified by densitometry.

DNA Oligomer Cleavage Assay

A single stranded DNA oligomer containing appropriate cleavage sites, for example the 22 mer GAATGAGCCG-CAACTTCGGGAT (SEQ ID NO: 3), or an appropriately labelled derivative, may be used as substrate. An appropriate label may be a radiolabel or a fluorescent chromophore attached at the 5' or 3' end of the oligo, according to the specific assay used. The substrate is incubated with a candidate inhibitor and a preparation of Topoisomerase III, in an appropriate buffer. The buffer may contain $Mg^{2+}$ or an alternative divalent metal ion. $Mg^{2+}$ is not essential for the cleavage reaction, although its inclusion may be desirable to facilitate the interaction of certain classes of inhibitors. The reaction is stopped by the addition of an appropriate denaturant, for example 1% SDS or 100 mM NaOH. Generation of the cleavable complex (stabilization of the key covalent reaction intermediate) may be measured by a number of methods. For example, electrophoresis using a denaturing polyacrylamide gel can be used to separate the 5' labelled cleaved DNA product which may then be quantified by densitometry. Alternatively, the 3' labelled DNA product may be assayed by virtue of its covalent association with Topoisomerase III. This may be performed by the SDS/K precipitation assay, in which radiolabelled DNA associated with precipitated protein is measured, or by a capture assay format in which Topoisomerase III is immobilized using an antibody and the amount of associated labelled DNA is measured.

Whole Cell Assays

Topoisomerase III-like effects of potential agonists and antagonists and poisons, may by measured, for instance, by determining activity of a reporter system that is sensitive to alterations in gene expression following interaction of the candidate molecule with a cell or appropriate cell preparation. Reporter systems that may be useful in this regard include but are not limited to colorimetric labeled substrate converted into product, a reporter gene that is responsive to changes in Topoisomerase III activity, and binding assays known in the art.

Potential antagonists include small organic molecules, peptides, polypeptides and antibodies that bind to a polypeptide of the invention and thereby inhibit or extinguish its activity, or stabilize the key covalent reaction intermediate with DNA. Potential antagonists also may be small organic molecules, a peptide, a polypeptide such as a closely related protein or antibody that binds the same sites on a binding molecule, such as a binding molecule, without inducing Topoisomerase III-induced activities, thereby preventing the action of Topoisomerase III by excluding Topoisomerase III from binding.

Potential antagonists include a small molecule which binds to and occupies the binding site of the polypeptide thereby preventing binding to cellular binding molecules, such as binding molecules, such that normal biological activity is prevented. Examples of small molecules include but are not limited to small organic molecules, peptides or peptide-like molecules.

Other potential antagonists include antisense molecules. Antisense technology can be used to control gene expression through antisense DNA or RNA or through double- or triple-helix formation. Antisense techniques are discussed, for example, in—Okano, J. Neurochem. 56:560 (1991); *OLIGODEOXYNUCLEOTIDES AS ANTISENSE INHIBITORS OF GENE EXPRESSION*, CRC Press, Boca Raton, Fla. (1988). Triple helix formation is discussed in, for instance Lee et al., *Nucleic Acids Research* 6:3073 (1979); Cooney et al., *Science* 241:456 (1988); and Dervan et al., *Science* 251:1360 (1991). The methods are based on binding of a polynucleotide to a complementary DNA or RNA. For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of Topoisomerase III. The antisense RNA oligonucleotide hybridizes to the mRNA in vivo and blocks translation of the mRNA molecule into Topoisomerase III polypeptide. The oligonucleotides described above can also be delivered to cells such that the antisense RNA or DNA may be expressed in vivo to inhibit production of Topoisomerase III.

Preferred potential antagonists include compounds related to and derivatives of each of the DNA sequences provided herein may be used in the discovery and development of antibacterial compounds. The encoded protein upon expression can be used as a target for the screening of antibacterial drugs. Additionally, the DNA sequences encoding the amino terminal regions of the encoded protein or Shine-Delgarno or other translation facilitating sequences of the respective mRNA can be used to construct antisense sequences to control the expression of the coding sequence of interest.

The antagonists and agonists of the invention may be employed in a composition with a pharmaceutically acceptable carrier, e.g., as hereinafter described.

The antagonists and agonists may be employed for instance to inhibit Streptococcal infections.

Vaccines

Another aspect of the invention relates to a method for inducing an immunological response in an individual, particularly a mammal which comprises inoculating the individual with Topoisomerase III, or a antigenic fragment or variant thereof, adequate to produce antibody to protect said individual from infection, particularly bacterial infection and most particularly Streptococcal infection. Yet another aspect of the invention relates to a method of inducing immunological response in an individual which comprises, through gene therapy, delivering gene encoding Topoisomerase III, or a antigenic fragment or a variant thereof, for expressing Topoisomerase III, or a fragment or a variant thereof in vivo in order to induce an immunological response to produce antibody to protect said individual from disease.

A further aspect of the invention relates to an immunological composition which, when introduced into a host capable or having induced within it an immunological response, induces an immunological response in such host to a Topoisomerase III or protein coded therefrom, wherein the composition comprises a recombinant Topoisomerase III or protein coded therefrom comprising DNA which codes for and expresses an antigen of said Topoisomerase III or protein coded therefrom.

The Topoisomerase III or a fragment thereof may be fused with co-protein which may not by itself produce antibodies, but is capable of stabilizing the first protein and producing a fused protein which will have immunogenic and protective properties. Thus fused recombinant protein, preferably further comprises an antigenic co-protein, such as Glutathione-S-transferase (GST) or beta-galactosidase, relatively large co-proteins which solubilise the protein and facilitate production and purification thereof. Moreover, the co-protein may act as an adjuvant in the sense of providing a generalized stimulation of the immune system. The co-protein may be attached to either the amino or carboxy terminus of the first protein.

The present invention also includes a vaccine formulation which comprises the immunogenic recombinant protein together with a suitable carrier. Since the protein may be broken down in the stomach, it is preferably administered parenterally, including, for example, administration that is subcutaneous, intramuscular, intravenous, or intradermal. Formulations suitable for parenteral administration include aqueous and non-aqueous sterile injection solutions which may contain anti-oxidants, buffers, bacteriostats and solutes which render the formulation instonic with the bodily fluid, preferably the blood, of the individual; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Whilst the invention has been described with reference to certain Topoisomerase III, it is to be understood that this covers fragments of the naturally occurring protein and similar proteins (for example, having sequence homologies of 50% or greater) with additions, deletions or substitutions which do not substantially affect the immunogenic properties of the recombinant protein.

Compositions

The invention also relates to compositions comprising the polynucleotide or the polypeptides discussed above or the agonists or antagonists. Thus, the polypeptides of the present invention may be employed in combination with a non-sterile or sterile carrier or carriers for use with cells, tissues or organisms, such as a pharmaceutical carrier suitable for administration to a subject. Such compositions comprise, for instance, a media additive or a therapeutically effective amount of a polypeptide of the invention and a pharmaceutically acceptable carrier or excipient. Such carriers may include, but are not limited to, saline, buffered saline, dextrose, water, glycerol, ethanol and combinations thereof. The formulation should suit the mode of administration.

Kits

The invention further relates to diagnostic and pharmaceutical packs and kits comprising one or more containers filled with one or more of the ingredients of the aforementioned compositions of the invention. Associated with such container(s) can be a notice in the form prescribed by a governmental agency regulating the manufacture, use or sale of pharmaceuticals or biological products, reflecting approval by the agency of the manufacture, use or sale of the product for human administration.

Administration

Polypeptides and other compounds of the present invention may be employed alone or in conjunction with other compounds, such as therapeutic compounds.

The pharmaceutical compositions may be administered in any effective, convenient manner including, for instance, administration by topical, oral, anal, vaginal, intravenous, intraperitoneal, intramuscular, subcutaneous, intranasal or intradermal routes among others.

The pharmaceutical compositions generally are administered in an amount effective for treatment or prophylaxis of a specific indication or indications. In general, the compositions are administered in an amount of at least about 10 $\mu$g/kg body weight. In most cases they will be administered in an amount not in excess of about 8 mg/kg body weight per day. Preferably, in most cases, dose is from about 10 $\mu$g/kg to about 1 mg/kg body weight, daily. It will be appreciated that optimum dosage will be determined by standard methods for each treatment modality and indication, taking into account the indication, its severity, route of administration, complicating conditions and the like.

In therapy or as a prophylactic, the active agent may be administered to an individual as an injectable composition, for example as a sterile aqueous dispersion, preferably isotonic.

Alternatively the composition may be formulated for topical application for example in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

For administration to mammals, and particularly humans, it is expected that the daily dosage level of the active agent will be from 0.01 mg/kg to 10 mg/kg, typically around 1 mg/kg. The physician in any event will determine the actual dosage which will be most suitable for an individual and will vary with the age, weight and response of the particular individual. The above dosages are exemplary of the average case. There can, of course, be individual instances where higher or lower dosage ranges are merited, and such are within the scope of this invention.

In-dwelling devices include surgical implants, prosthetic devices and catheters, i.e., devices that are introduced to the body of an individual and remain in position for an extended time. Such devices include, for example, artificial joints, heart valves, pacemakers, vascular grafts, vascular catheters, cerebrospinal fluid shunts, urinary catheters, continuous ambulatory peritoneal dialysis (CAPD) catheters, etc.

The composition of the invention may be administered by injection to achieve a systemic effect against relevant bacteria shortly before insertion of an in-dwelling device. Treatment may be continued after surgery during the in-body time of the device. In addition, the composition could also be used to broaden perioperative cover for any surgical technique to prevent Streptococcal wound infections.

Many orthopedic surgeons consider that humans with prosthetic joints should be considered for antibiotic prophylaxis before dental treatment that could produce a bacteraemia. Late deep infection is a serious complication sometimes leading to loss of the prosthetic joint and is accompanied by significant morbidity and mortality. It may therefore be possible to extend the use of the active agent as a replacement for prophylactic antibiotics in this situation.

In addition to the therapy described above, the compositions of this invention may be used generally as a wound treatment agent to prevent adhesion of bacteria to matrix proteins exposed in wound tissue and for prophylactic use in dental treatment as an alternative to, or in conjunction with, antibiotic prophylaxis.

Alternatively, the composition of the invention may be used to bathe an indwelling device immediately before insertion. The active agent will preferably be present at a concentration of 1 µg/ml to 10 mg/ml for bathing of wounds or indwelling devices.

A vaccine composition is conveniently in injectable form. Conventional adjuvants may be employed to enhance the immune response.

A suitable unit dose for vaccination is 0.5–5 microgram/kg of antigen, and such dose is preferably administered 1–3 times and with an interval of 1–3 weeks.

With the indicated dose range, no adverse toxicological effects will be observed with the compounds of the invention which would preclude their administration to suitable individuals.

The antibodies described above may also be used as diagnostic reagents to detect the presence of bacteria containing Topoisomerase.

Each reference disclosed herein is incorporated by reference herein in its entirety. Any patent application to which this application claims priority is also incorporated by reference herein in its entirety.

In order to facilitate understanding of the following example certain frequently occurring methods and/or terms will be described.

EXAMPLES

The present invention is further described by the following examples. The examples are provided solely to illustrate the invention by reference to specific embodiments. These exemplification's, while illustrating certain specific aspects of the invention, do not portray the limitations or circumscribe the scope of the disclosed invention.

Certain terms used herein are explained in the foregoing glossary.

All examples were carried out using standard techniques, which are well known and routine to those of skill in the art, except where otherwise described in detail. Routine molecular biology techniques of the following examples can be carried out as described in standard laboratory manuals, such as Sambrook et al., *MOLECULAR CLONING: A LABORATORY MANUAL,* 2nd Ed.; Cold Spring Harbor Laboratory Press, Cold Spring Harbor, N.Y. (1989).

All parts or amounts set out in the following examples are by weight, unless otherwise specified.

Unless otherwise stated size separation of fragments in the examples below was carried out using standard techniques of agarose and polyacrylamide gel electrophoresis ("PAGE") in Sambrook et al., *MOLECULAR CLONING: A LABORATORY MANUAL,* 2nd Ed., Cold Spring Harbor Laboratory Press, Cold Spring Harbor, N.Y. (1989) and numerous other references such as, for instance, by Goeddel et al., *Nucleic Acids Res.* 8:4057 (1980).

Unless described otherwise, ligations were accomplished using standard buffers, incubation temperatures and times, approximately equimolar amounts of the DNA fragments to be ligated and approximately 10 units of T4 DNA ligase ("ligase") per 0.5 microgram of DNA.

The polynucleotide having the DNA sequence given in (SEQ ID NO: 1) was obtained from the sequencing of a library of clones of chromosomal DNA of *Streptococcus pneumoniae* 0100993 in *E. coli.*

To obtain the polynucleotide encoding the Topoisomerase III protein using the DNA sequence given in (SEQ ID NO: 1) typically a library of clones of chromosomal DNA of *Streptococcus pneumoniae* 0100993 in *E. coli* or some other suitable host is probed with a radiolabelled oligonucleotide, preferably a 17mer or longer, derived from the partial sequence. Clones carrying DNA identical to that of the probe can then be distinguished using high stringency washes. By sequencing the individual clones thus identified with sequencing primers designed from the original sequence it is then possible to extend the sequence in both directions to determine the full gene sequence. Conveniently such sequencing is performed using denatured double stranded DNA prepared from a plasmid clone. Suitable techniques are described by Maniatis, T., Fritsch, E. F. and Sambrook et al., *MOLECULAR CLONING, A LABORATORY MANUAL,* 2nd Ed.; Cold Spring Harbor Laboratory Press, Cold Spring Harbor, N.Y. (1989). (see Screening By Hybridization 1.90 and Sequencing Denatured Double-Stranded DNA Templates 13.70).

Example 1

Isolation of DNA Coding for Novel Topoisomerase III Protein from *Streptococcus Pneumoniae*

The polynucleotide having the DNA sequence given in (SEQ ID NO: 1) was obtained from a library of clones of chromosomal DNA of *Streptococcus pneumoniae* in *E.coli.* In some cases the sequencing data from two or more clones containing overlapping *Streptococcus pneumoniae* DNA was used to construct the contiguous DNA sequence in (SEQ ID NO: 1). Libraries may be prepared Libraries may be prepared by routine methods, for example, Methods 1 and 2 below.

Total cellular DNA is isolated from *Streptococcus pneumoniae* strain 0100993 according to standard procedures and size-fractionated by either of two methods.

Method 1

Total cellular DNA is mechanically sheared by passage through a needle in order to size-fractionate according to standard procedures. DNA fragments of up to 11 kbp in size are rendered blunt by treatment with exonuclease and DNA polymerase, and EcoRI linkers added. Fragments are ligated into the vector Lambda ZapII that has been cut with EcoRI, the library packaged by standard procedures and *E.coli* infected with the packaged library. The library is amplified by standard procedures.

Method 2

Total cellular DNA is partially hydrolysed with a combination of four restriction enzymes (RsaI, PalI, AluI and Bsh1235I ) and size-fractionated according to standard procedures. EcoRI linkers are ligated to the DNA and the fragments then ligated into the vector Lambda ZapII that have been cut with EcoRI, the library packaged by standard procedures, and *E.coli* infected with the packaged library. The library is amplified by standard procedures.

---

What is claimed is:

1. An isolated polynucleotide segment comprising: a first polynucleotide sequence, wherein the first polynucleotide sequence (a) is a reference sequence that encodes the amino acid sequence set forth in SEQ ID NO:2, or (b) has at least 95% identity with the reference sequence, wherein identity is determined using an algorithm consisting of BLASTN, where the algorithm is adapted to give the largest match between sequences tested, over the entire length of the reference sequence.

2. An isolated polynucleotide segment according to claim 1 comprising: a first polynucleotide sequence, wherein the first polynucleotide sequence (a) encodes a reference sequence that has the amino acid sequence set forth in SEQ ID NO:2, or (b) encodes a polypeptide sequence identical with the reference sequence except that, over the entire length corresponding to the reference sequence, the encoded polypeptide sequence has up to ten amino acid substitutions, amino acid deletions or amino acid insertions.

3. The isolated polynucleotide segment of claim 1, comprising the first polynucleotide sequence wherein the first polynucleotide sequence is (a) identical with the reference sequence, or (b) has at least 97% identity with the reference sequence, wherein identity is determined using an algorithm consisting of BLASTN, where the algorithm is adapted to give the largest match between sequences tested, over the entire length of the reference sequence.

4. The isolated polynucleotide segment of claim 1, wherein the first polynucleotide sequence encodes a Topoisomerase III polypeptide.

5. An isolated polynucleotide segment comprising the full complement of the entire length of the first polynucleotide sequence of claim 1.

6. The isolated polynucleotide segment of claim 1, wherein the isolated polynucleotide comprises the complement sequence, which is the complement of the first polynucleotide sequence wherein the first polynucleotide sequence (a) encodes a reference sequence that has the amino acid sequence set forth in SEQ ID NO:2, or (b) encodes a polypeptide sequence identical with the reference sequence except that, over the entire length corresponding to the reference sequence, the encoded polypeptide sequence has up to five amino acid substitutions, amino acid deletions or amino acid insertions.

7. The isolated polynucleotide segment of claim 5, wherein the first polynucleotide sequence encodes a Topoisomerase III polypeptide.

8. A vector comprising the polynucleotide segment of claim 1.

9. An isolated host cell transfected with the isolated polynucleotide segment of claim 1 to express the first polynucleotide sequence.

10. A process for producing a Topoisomerase III polypeptide comprising the step of culturing the host cell of claim 9 under conditions sufficient for the production of said polypeptide.

11. An isolated polynucleotide segment comprising a first polynucleotide sequence, wherein the first polynucleotide sequence is (a) a reference sequence which encodes the same mature polypeptide, expressed by the Topoisomerase III gene contained in Streptococcus pneumoniae 0100993 contained in NCIMB Deposit No. 40794, or (b) has at least 95% identity with the reference sequence, wherein identity is determined using an algorithm consisting of BLASTN, where the algorithm is adapted to give the largest match between sequences tested, over the entire length of the reference sequence.

12. An isolated polynucleotide segment of claim 11, wherein the first polynucleotide sequence is (a) the reference sequence, or (b) has at least 97% identity with the reference sequence, wherein identity is determined using an algorithm consisting of BLASTN, where the algorithm is adapted to give the largest match between sequences tested, over the entire length of the reference sequence.

13. An isolated polynucleotide segment of claim 11 wherein the first polynucleotide sequence encodes the same mature polypeptide expressed by the Topoisomerase III gene contained in Streptococcus pneumoniae 0100993 contained in NCIMB Deposit No. 40794, or the full complement of the entire length of the first polynucleotide sequence.

14. A polynucleotide which encodes a fusion polypeptide and which includes the isolated polynucleotide segment according to claim 11.

15. A recombinant polynucleotide segment comprising nucleotides 1 to 441 of the polynucleotide sequence set forth in SEQ ID NO:1, or the full complement of the entire length of nucleotides 1 to 441 set forth in SEQ ID NO:1.

16. A recombinant polynucleotide segment which encodes a polypeptide comprising a region having the amino acid sequence of SEQ ID NO:2.

17. A vector comprising the recombinant polynucleotide segment of claim 16.

18. An isolated host cell transfected with the recombinant polynucleotide segment of claim 16 to express the recombinant polynucleotide segment.

19. A process for producing a Topoisomerase III polypeptide of the recombinant polynucleotide segment comprising the step of culturing the host cell of claim 18 under conditions sufficient for the production of said polypeptide, which is encoded by the recombinant polynucleotide segment.

20. An isolated polynucleotide comprising:
(a) a first polynucleotide sequence, wherein the first polynucleotide sequence is selected from the group consisting of:
  (i) a first reference sequence which encodes the amino acid sequence set forth in SEQ ID NO:2;
  (ii) a second reference sequence which is nucleotides 1 to 441 set forth in SEQ ID NO:1;
  (iii) a third reference sequence which comprises at least 50 sequential bases of the first reference sequence or the second reference sequence; and
  (iv) a fourth reference sequence which comprises at least 30 sequential bases of the first reference sequence or the second reference sequence; or
(b) the full complement of the first polynucleotide sequence.

21. The isolated polynucleotide of claim 20 wherein the first polynucleotide sequence is DNA or RNA.

22. A vector comprising the isolated polynucleotide of claim 21.

23. An isolated host cell comprising the vector of claim 22.

24. A process for producing a Topoisomerase III polypeptide of the recombinant polynucleotide segment comprising the step of culturing the host cell of claim 23 under conditions sufficient for the production of said polypeptide, which is encoded by the recombinant polynucleotide segment.

25. The isolated polynucleotide of claim 20, wherein the first polynucleotide sequence comprises at least 50 sequential bases of the first reference sequence.

26. The isolated polynucleotide of claim 25 wherein the first polynucleotide sequence is DNA or RNA.

27. A vector comprising the isolated polynucleotide of claim 26.

28. An isolated host cell comprising the vector of claim 27.

29. A process for producing a Topoisomerase III polypeptide of the recombinant polynucleotide segment comprising the step of culturing the host cell of claim 28 under conditions sufficient for the production of said polypeptide, which is encoded by the recombinant polynucleotide segment.

* * * * *

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 442 base pairs
      (B) TYPE: nucleic acid
      (C) STRANDEDNESS: single
      (D) TOPOLOGY: linear (ii) MOLECULE TYPE: Genomic DNA (xi) SEQUENCE DESCRIPTION: SEQ ID NO:1:

```
GATGTTCGTT GAAGCCGAAC TGAAGCCGAC CGGTCTGGAG CGAGCCGAAG CCCAGGCCAT      60

CGCCGACGCG GTGCGCAACC AGACCGGCAC CGTCACCGAA GAAGCCAAGC CCAGCACGCA     120

GGCCAGCCCG TTGCTGTACG ACCTGACCAC GCTGCAACGC GAAGCCAACT CGCGCTTCGG     180

CTTCAGCGCC AAGACCACGC TGTCGCTGGC ACAGGCGCTA TACGAAAAAC ACAAGGCGCT     240

GACCTACCCG CGGACCGATT CACGCGCCCT GCCTGAAGAC TACCTGGGCG TGGTCAAGCA     300

GACCGTCGGC GTGCTGGCCG AGGGCGACCT GCCCGGCCCG CTGAAGGCTT TGTCGGCTCA     360

CGCCGAAAAG GCGCTGAAAG AGGGTTACAT CAAACCCAAC AAGCGCGTGT TCGACAACGC     420

CAAGGTGTCG GACCACTTCG CC                                             442
```

(2) INFORMATION FOR SEQ ID NO:2:

(i) SEQUENCE CHARACTERISTICS:
      (A) LENGTH: 148 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:2:

```
Met Phe Val Glu Ala Glu Leu Lys Pro Thr Gly Leu Glu Arg Ala Glu
1               5                  10                  15

Ala Gln Ala Ile Ala Asp Ala Val Arg Asn Gln Thr Gly Thr Val Thr
            20                  25                  30

Glu Glu Ala Lys Pro Ser Thr Gln Ala Ser Pro Leu Leu Tyr Asp Leu
        35                  40                  45

Thr Thr Leu Gln Arg Glu Ala Asn Ser Arg Phe Gly Phe Ser Ala Lys
    50                  55                  60

Thr Thr Leu Ser Leu Ala Gln Ala Leu Tyr Glu Lys His Lys Ala Leu
65                  70                  75                  80

Thr Tyr Pro Arg Thr Asp Ser Arg Ala Leu Pro Glu Asp Tyr Leu Gly
                85                  90                  95
```

```
Val Val Lys Gln Thr Val Gly Val Leu Ala Glu Gly Asp Leu Pro Gly
            100                 105                 110

Pro Leu Lys Ala Leu Ser Ala His Ala Glu Lys Ala Leu Lys Glu Gly
            115                 120                 125

Tyr Ile Lys Pro Asn Lys Arg Val Phe Asp Asn Ala Lys Val Ser Asp
        130                 135                 140

His Phe Ala
145

(2) INFORMATION FOR SEQ ID NO:3:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:3:

GAATGAGCCG CAACTTCGGG AT                                              22
```